United States Patent
Keenan et al.

[11] Patent Number: 6,092,567
[45] Date of Patent: Jul. 25, 2000

[54] APPARATUS FOR PRODUCING A PHARMACEUTICAL PRODUCT

[75] Inventors: David Keenan; Padraig Somers, both of Dublin, Ireland

[73] Assignee: Helsinn Chemicals Ireland Limited, Dublin, Ireland

[21] Appl. No.: 09/189,869

[22] Filed: Nov. 12, 1998

[30] Foreign Application Priority Data

Nov. 11, 1997 [IE] Ireland ..................................... 970801

[51] Int. Cl.⁷ .................................................. A61K 9/16
[52] U.S. Cl. .............................................. 141/69; 141/11
[58] Field of Search ......................................... 141/11, 69

[56] References Cited

U.S. PATENT DOCUMENTS

| | | | |
|---|---|---|---|
| 3,480,597 | 11/1969 | Korshak | 260/78.5 |
| 4,115,107 | 9/1978 | Booz et al. | 75/0.5 |
| 4,849,227 | 7/1989 | Cho | 424/498 |
| 5,354,562 | 10/1994 | Platz et al. | 424/489 |
| 5,715,646 | 2/1998 | Smekens | 53/121 |
| 5,747,002 | 5/1998 | Clark et al. | 424/45 |
| 5,769,571 | 6/1998 | Higuchi | 406/137 |

FOREIGN PATENT DOCUMENTS

| | | |
|---|---|---|
| 0604034 | 6/1994 | European Pat. Off. . |
| 3438310 | 4/1986 | Germany . |

*Primary Examiner*—J. Casimer Jacyna
*Attorney, Agent, or Firm*—Jacobson, Price, Holman & Stern, PLLC

[57] ABSTRACT

A method and apparatus for producing a pharmaceutical product in a micronised form. The pharmaceutical product is delivered at a predetermined flow rate from a gravimetric feeding device into a delivery line. An air compressor generates an air stream which is delivered along an airline into which the pharmaceutical product delivery line is discharged for delivering the product to a microniser which micronises the product to a desired size range. The micronised product is delivered through a cyclone filter apparatus from which the micronised product is collected through an outlet valve to a storage drum.

15 Claims, 1 Drawing Sheet

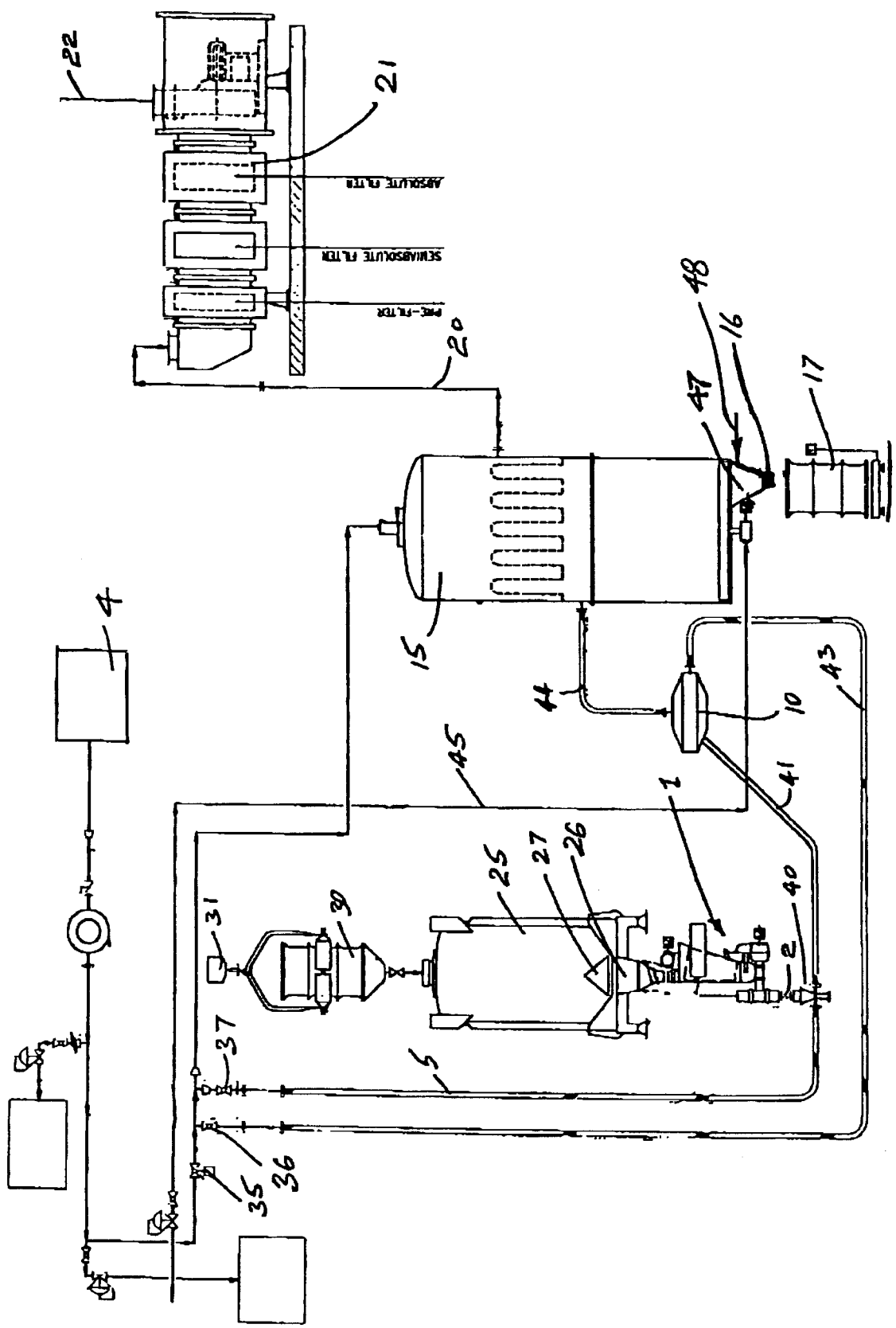

APPARATUS FOR PRODUCING A PHARMACEUTICAL PRODUCT

BACKGROUND OF THE INVENTION

The invention relates to a method and apparatus for producing a pharmaceutical product and in particular to a method and apparatus for producing a pharmaceutical product in a micronised form.

It is often necessary to produce a pharmaceutical product in a micronised form for a number of reasons, for example to enable the product to be formulated in a pharmaceutical composition for administering to humans.

One such pharmaceutical product is nimesulide as described in U.S. Pat. No. 3,480,597. Nimesulide is a non-steroidal anti-inflammatory medicament that is useful in a range of treatments such as in treating chronic rheumatoid arthritis or osteoarthritis.

In order to improve the solubility of nimesulide in the stomach, smaller particle size ranges of the active ingredient are required than has heretofore been possible using conventional processing techniques.

There is therefore a need for a method and apparatus for producing a pharmaceutical product, especially nimesulide, in a micronised form.

SUMMARY OF THE INVENTION

According to the invention, there is provided a method for producing a pharmaceutical product in a micronised form comprising the steps of:

delivering a particulate pharmaceutical product in a flowable form into a feeding device;

feeding a predetermined flow rate of the pharmaceutical product from the feeding device into a controlled air stream;

delivering the air stream containing the product to a microniser;

micronising the product to a desired size in the microniser; and collecting the micronised product of the desired size.

In a particularly preferred embodiment of the invention, the process includes feeding the product from the feeding device into the controlled air stream by a venturi device.

In an especially preferred embodiment of the invention, the process includes controlling the pressure of the air stream such that it lies within a preset desirable pressure range.

In a particularly preferred embodiment of the invention, the process includes controlling the temperature of the air stream such that it lies within a preset desirable temperature range.

In one embodiment of the invention, the method includes the steps of:

loading the product into an intermediate bulk container having an outlet which is normally obdurated by a closure device to maintain the product in the container; and opening the closure device to discharge the product on demand to the feeding device.

In this case, preferably the method includes the step of vibrating the product required for assisting delivery of product on demand to the feeding device.

In a particularly preferred arrangement, the feeding device is a gravimetric feeding device and the method includes the step of weighing the product and delivering a controlled predetermined feedrate of the product into the air stream, on demand.

In one arrangement, the micronised product is collected by passing the micronised product entrained in an air stream through a filter apparatus which separates the micronised product into an air stream and a main product stream containing the micronised product with the desired particle size range. In this case, preferably the method includes the step of filtering the air stream by passing the air stream through a hepafilter to substantially remove fines prior to discharge. In a particularly preferred arrangement, in this case the method includes the step of disabling the flow of air if the path through the hepafilter is blocked.

Conveniently, the method of the invention includes the step of injecting a gas stream into the micronised product as it is being discharged from the filter apparatus. This advantageously fluidises the powder to facilitate subsequent handling of the product The gas stream may be air or nitrogen.

In another aspect, the invention provides an apparatus for producing a pharmaceutical product in a micronised form comprising:

a feeding device for a particulate pharmaceutical product;

the feeding device having a product inlet and a product outlet;

the feeding device operable to discharge particulate pharmaceutical product through the outlet at a predetermined flow rate;

a microniser for micronising the product to a desired particle size;

the microniser having an inlet and an outlet;

a pharmaceutical product delivery line communicating between the feeder outlet and the microniser inlet;

means for generating an air stream and delivering said air stream through the pharmaceutical product delivery line between the feeder outlet and the microniser inlet;

means for controlling the air stream; and means for collecting the micronised product.

Most preferably, a venturi device is mounted in the pharmaceutical product delivery line at the feeder outlet for delivery of particulate pharmaceutical product from the feeder device into the pharmaceutical delivery line.

In a particularly preferred embodiment of the invention, the control means includes means for controlling the pressure of the air stream.

In an especially preferred embodiment of the invention, the control means includes means fore controlling the temperature of the air stream.

In one embodiment of the invention, the apparatus includes an intermediate bulk container having an outlet which is normally obdurated by a closure device to maintain the product in the container, means for opening the closure device to deliver the product to the feeding device on demand. In this case preferably the apparatus includes vibrating means for vibrating the product as required to provide delivery of the product from the intermediate bulk container to the feeding device.

In one arrangement, the feeding device is a gravimetric feeding device to weigh the product and deliver a predetermined controlled feedrate of the product into the air stream, on demand.

In a particularly preferred embodiment of the invention, the collecting means comprises a filter apparatus for separating the micronised product entrained in an air stream into an air stream and a main product stream containing the micronised product of a desired particle size.

Most preferably, the apparatus includes a hepafilter for filtering the air stream to remove fines.

Conveniently, the apparatus includes means at an outlet of the filter apparatus for injecting an air stream into the micronised product as it passes through the outlet.

The invention also provides a pharmaceutical product, particularly nimesulide, in a micronised form whenever produced by a method and/or using an apparatus of the invention.

BRIEF DESCRIPTION OF THE DRAWINGS

FIG. 1 is a diagram illustrating the method and apparatus of the invention.

DETAILED DESCRIPTION

Referring to the drawing, there is illustrated an apparatus for producing a pharmaceutical product, in this case, nimesulide, in a micronised form. The apparatus comprises a feeding device indicated generally by the reference numeral 1 for delivering a predetermined flowrate of the pharmaceutical product into a delivery line 2. A compressor 4 generates an air stream which is delivered along an air line 5 into which the pharmaceutical product delivery line 2 is discharged for delivering the product to a microniser 10 which micronises the product to a desired size range. The micronised product from the microniser 10 is collected by a collecting means, in this case in the form of a cyclone 15 filter apparatus, from which the micronised product is collected through an outlet valve 16 to a storage drum 17. The cyclone 15 separates the micronised product into a product stream containing the pharmaceutical product in the desired particle size range and an air stream which is delivered along a line 20 to a hepafilter 21 for filtering any fines from the air stream prior to discharge of the air through a discharge air outlet 22.

In this case, the feeding device 1 is a gravimetric feeding device for delivering a predetermined flow rate of the pharmaceutical product. One such feeding device is available under the trade name K-TRON. The pharmaceutical product is delivered to the feeding device 1 from an intermediate bulk container 25 having an outlet 26 which is normally obdurated by a closure device 27 to maintain the product in the container 25. The closure device 27 is opened to deliver the product to the feeding device 1 on demand. One such intermediate bulk container system is available under the trade name MATCON. Typically, the pharmaceutical product is loaded into the intermediate bulk container 25 from a drum 30 which is delivered to the top of the container 25 by a hoist 31.

Control means for controlling the air stream from the compressor 4 in this case includes an air control valve 35 which is used to regulate the pressure of the air stream. Manual valves 36, 37 downstream of the control valve 35 may also be used to further regulate the flow of air to a venturi 40 and microniser 10.

Delivery means for delivering the air stream containing the product from the feeding device 1 to the microniser 10 in this case comprises a venturi device 40 which is fed with the product from the feeding device 1 along the delivery line 2 and with air along the air line 5. The venturi device 40 functions to entrain the pharmaceutical product in the air stream for delivery along a pharmaceutical product delivery line 41 to the microniser 10. Air for the microniser 10 is delivered downstream of the control valve 35 along a microniser air supply line 43. Micronised product from the microniser 10 is entrained in the air which is delivered along a cyclone feed line 44 to the cyclone 15. Input air to the cyclone 15 is delivered along a cyclone air line 45.

In operation, coarse particulate pharmaceutical product in a flowable form is delivered from a drum 30 into the intermediate bulk container 25. The flow of product from the container 25 is controlled by opening and closing the closure device 27. If required, the container 25 and/or outlet 26 is vibrated to release the product from the container 25 to ensure flow of the product on demand.

The product is delivered into the feeding device 1 which delivers a predetermined flow rate of the product to the venturi 40. The controlled air supply to the venturi 40 delivers the pharmaceutical product in a controlled predictable and optimised manner to the microniser 10. The air supply along the line 43 to the microniser 10 is also controlled and predictable so that the micronising process is also optimised. Thus, the stream of micronised pharmaceutical product entrained in the air exiting the microniser along the exit line 44 has an optimised particle size range. The amount of fines in the air steam 20 from the cyclone 15 is minimised while the yield of micronised product from the cyclone 15 collected in the container 17 is optimised. Any fines in the air stream 20 are removed by the hepafilter 21 prior to discharge of the air through the outlet discharge line 22.

Preferably, as the micronised product is discharged through an outlet 47 at a bottom of the cyclone 15, an air stream 48 is injected into the outlet 47 to fluidise the micronised pharmaceutical product powder to facilitate subsequent handling of the product. Nitrogen may be injected instead of air.

Typically, the pharmaceutical product has a coarse particle size of 70 $\mu$m at the intermediate bulk container 25 prior to processing. Downstream of the microniser 10, the product has a particle size less than 12 $\mu$m.

It may in some cases be desirable to cool the coarse particulate pharmaceutical product prior to delivery into the microniser. This cooling would promote better break-down of the product particles in the microniser as the cooled particles would be more brittle. This cooling may conveniently be achieved by cooling the controlled air stream upstream of the venturi device.

The invention provides an optimised method and apparatus for producing a pharmaceutical product, especially nimesulide, in a micronised form Because of the optimisation of the process, the final product has a particular specification with an optimised size range which allows the product to be readily formulated into pharmaceutical compositions which optmise the absorption of the active ingredient on administration.

The invention is not limited to the embodiments hereinbefore described which may be varied in both construction and detail.

What is claim is:

1. A method for producing a pharmaceutical product in a micronised form comprising the steps of:

weighing and delivering a particulate pharmaceutical product in a flowable form into a gravimetric feeding device;

feeding a predetermine flow rate of the pharmaceutical product form the feeding device into a controlled air stream;

delivering the air stream containing the product to a microniser;

micronising the product to a desired size in the microniser, passing the micronised product through a filter apparatus to separate the micronised product into an air stream and a main product stream containing the micronised product with the desired particle size range; and collecting the micronised product of the desired size.

2. A method as claimed in claim 1, which includes feeding the product from the gravimetric feeding device into the controlled air stream by a venturi device.

3. A method as claimed in claim 1, which includes controlling the pressure of the air stream such that it lies within a preset desirable pressure range.

4. A method as claimed in claim 1, including the steps of:

loading the product into an intermediate bulk container having an outlet which is normally obdurated by a closure device to maintain the product in the container; and opening the closure device to discharge the product on demand to the gravimetric feeding device.

5. A method as claimed in claim 4, including the step of vibrating the product as required to provide delivery of product on demand to the gravimetric feeding device.

6. A method as claimed in claim 1, which includes the step of injecting a gas stream into the micronised product as it is being discharged from the filter apparatus.

7. A method as claimed in claim 1, wherein the pharmaceutical product is nimesulide.

8. A pharmaceutical product whenever produced by a method as claimed in claim 1.

9. Apparatus for producing a pharmaceutical product in a micronised from comprising:

a gravimetric feeding device for a particulate pharmaceutical product;

the gravimetric feeding device having a product inlet and a product outlet;

the gravimetric feeding device operable to discharge particulate pharmaceutical product through the outlet at a predetermined flow rate;

a microniser for micronising the product to a desired particle size;

the microniser having an inlet and an outlet;

a pharmaceutical product delivery line communicating between the feeder outlet and the microniser inlet;

means for generating an air stream and delivering said air stream through the pharmaceutical product delivery line between the feeder outlet and the microniser inlet;

means for controlling the air stream; and a filter apparatus for separating the micronised product entrained in an air stream into an air stream and a main product stream containing the micronised product of a desired particle size.

10. Apparatus as claimed in claim 9, wherein a venturi device is mounted in the pharmaceutical product delivery line at the feeder outlet for delivery of particulate pharmaceutical product from the gravimetric feeder device into the pharmaceutical delivery line.

11. Apparatus as claimed in claim 9, wherein the control means includes means for controlling the pressure of the air stream.

12. Apparatus as claimed in claim 9, including an intermediate bulk container having an outlet which is normally obdurated by a closure device to maintain the product in the container means for opening, the closure device to deliver the product to the gravimetric feeding device on demand.

13. Apparatus as claimed in claim 12, including vibrating means for vibrating the product as required to provide delivery of the product from the intermediate bulk container to the feeding device.

14. Apparatus as claimed in claim 9, wherein the gravimetric feeding device weighs the product and delivers a predetermined controlled feedrate of the product into the air stream, on demand.

15. Apparatus as claimed in claim 10 having means at an outlet of the filter apparatus for injecting a gas stream into the micronised product as it passes through the outlet.

* * * * *